(12) United States Patent
Nakamura et al.

(10) Patent No.: US 11,839,468 B2
(45) Date of Patent: Dec. 12, 2023

(54) COMPONENT CONCENTRATION MEASUREMENT DEVICE AND COMPONENT CONCENTRATION MEASUREMENT METHOD

(71) Applicant: Nippon Telegraph and Telephone Corporation, Tokyo (JP)

(72) Inventors: Masahito Nakamura, Tokyo (JP); Takuro Tajima, Tokyo (JP); Michiko Seyama, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 425 days.

(21) Appl. No.: 17/048,343

(22) PCT Filed: Apr. 11, 2019

(86) PCT No.: PCT/JP2019/015751
§ 371 (c)(1),
(2) Date: Oct. 16, 2020

(87) PCT Pub. No.: WO2019/203110
PCT Pub. Date: Oct. 24, 2019

(65) Prior Publication Data
US 2021/0177310 A1   Jun. 17, 2021

(30) Foreign Application Priority Data
Apr. 20, 2018   (JP) .................................. 2018-081175

(51) Int. Cl.
*A61B 5/1455* (2006.01)
*A61B 5/1495* (2006.01)
(Continued)

(52) U.S. Cl.
CPC .......... *A61B 5/1455* (2013.01); *A61B 5/1495* (2013.01); *A61B 5/14532* (2013.01); *A61B 5/4875* (2013.01); *A61B 2562/0271* (2013.01)

(58) Field of Classification Search
CPC ....... A61B 5/01; A61B 5/1455; A61B 5/1495; A61B 5/14532; A61B 5/4875; A61B 2562/0271
See application file for complete search history.

(56) References Cited

U.S. PATENT DOCUMENTS

2006/0061371 A1   3/2006 Inoue et al.
2007/0197886 A1*  8/2007 Naganuma ......... A61B 5/14532
                                                              600/316
(Continued)

FOREIGN PATENT DOCUMENTS

| JP | 2004150960 A | 5/2004 |
| JP | 2016188778 A | 11/2016 |
| WO | 2007145143 A1 | 12/2007 |

OTHER PUBLICATIONS

Gustavo Guarin et al., "Miniature Microwave Biosensors," IEEE Microwave Magazine, Mar. 2015, pp. 71-86.

*Primary Examiner* — Devin B Henson
*Assistant Examiner* — Jonathan M Haney
(74) *Attorney, Agent, or Firm* — Slater Matsil, LLP

(57) ABSTRACT

A component concentration measuring apparatus includes: a dielectric spectroscopy portion that irradiates a measurement subject with electromagnetic waves and measures a complex permittivity, thereby acquiring a dielectric spectroscopy spectrum; a temperature measurement portion that measures a temperature of the measurement subject; a signal processing portion that corrects the dielectric spectroscopy spectrum according to the temperature measured by the temperature measurement portion; and a calculating portion that applies a calibration model generated in advance from
(Continued)

a dielectric spectroscopy spectrum of a sample whose component concentration is known, to the dielectric spectroscopy spectrum corrected by the signal processing portion, thereby calculating a component concentration of the measurement subject. A dielectric spectroscopy sensor that transmits and receives electromagnetic waves and a temperature sensor that outputs a signal that changes in accordance with a temperature are fixed to the measurement probe such that a certain distance is interposed between the sensors.

16 Claims, 11 Drawing Sheets

(51) Int. Cl.
*A61B 5/145* (2006.01)
*A61B 5/00* (2006.01)

(56) References Cited

U.S. PATENT DOCUMENTS

| | | | |
|---|---|---|---|
| 2009/0275814 A1 | 11/2009 | Watanabe et al. | |
| 2013/0211214 A1* | 8/2013 | Olsen | G16H 50/20 600/323 |
| 2020/0113495 A1* | 4/2020 | Feldman | A61B 5/14532 |
| 2022/0326212 A1* | 10/2022 | Potyrailo | B61L 3/002 |

* cited by examiner

COMPONENT CONCENTRATION MEASUREMENT DEVICE AND COMPONENT CONCENTRATION MEASUREMENT METHOD

CROSS-REFERENCE TO RELATED APPLICATIONS

This application is a national phase entry of PCT Application No. PCT/JP2019/015751, filed on Apr. 11, 2019, which claims priority to Japanese Application No. 2018-081175, filed on Apr. 20, 2018, which applications are hereby incorporated herein by reference.

TECHNICAL FIELD

The present invention relates to a technique for measuring a component concentration of a component of interest, using the dielectric spectroscopic technique.

BACKGROUND

Recently, demand is on the rise for wearable terminals in the health care field, and development of techniques for measuring various types of medical information with ease is in demand. As the measurement subject, blood components such as a blood glucose level, a water content of the skin, and the like are conceivable. For example, tests of a blood glucose level and the like involve drawing blood, and thus they significantly stress patients. Thus, non-invasive component concentration measuring methods not involving drawing blood have been gaining attention.

As non-invasive component concentration measuring methods, some methods using electromagnetic waves in microwave to millimeter-wave bands have been proposed because scattering is unlikely to occur in a living body compared with optical techniques using near infrared light or the like, and the energy in one photon is low, for example. For example, in the method disclosed in NPL 1, frequency characteristics around the resonance frequency are measured by bringing a device with a high Q factor such as an antenna or a resonator into contact with a sample that is to be measured. The resonance frequency is determined by a complex permittivity around a device, and thus, according to methods for measuring the shift amount of the resonance frequency, a correlation between shift amounts and component concentrations is measured in advance, and a component concentration is estimated from a shift amount of a resonance frequency.

As another component concentration measuring method using electromagnetic waves in microwave to millimeter-wave bands, a dielectric spectroscopic technique has been proposed (PL 1). According to the dielectric spectroscopic technique, the subcutaneous part is irradiated with electromagnetic waves, electromagnetic waves are allowed to be absorbed according to the interaction between a blood component that is a measurement subject, such as a glucose molecule, and water, and the amplitude and the phase of electromagnetic waves are observed. A dielectric relaxation spectrum is calculated from the amplitude or the phase of a signal corresponding to the frequency of observed electromagnetic waves. Typically, a dielectric relaxation spectrum is expressed in the form of linear combination of relaxation curves based on the Cole-Cole plot, and is used to calculate complex permittivity. The complex permittivity has a correlation, for example, with the amount of blood component such as glucose or cholesterol contained in blood in measurement of biological components, and is measured as an electrical signal (amplitude, phase) corresponding to a change thereof. A calibration model is constructed by measuring in advance a correlation between changes in complex permittivity and component concentrations, and calibration of the component concentration is performed from a change in the measured dielectric relaxation spectrum.

The dielectric spectroscopic technique measures a spectrum obtained by overlapping spectra unique to substances, and thus a feature amount unique to a measurement subject can be extracted using a statistical multivariate analysis method. Accordingly, this technique is superior to the resonator technique disclosed in NPL 1, regarding component concentration measurement in a multi-component system such as a blood system.

Furthermore, it is also possible to measure the water content in a living body, by performing component analysis regarding water using the dielectric spectroscopic technique, that is, dielectric spectroscopy is a technique that can be applied to both of component analysis and water content measurement.

However, the dielectric spectroscopic technique is problematic in that a dielectric spectroscopy spectrum changes in accordance with a change in the temperature of a measurement subject during measurement of the component concentration, which leads to a decrease in the level of measurement precision.

CITATION LIST

Patent Literature

PTL 1—Japanese Patent Application Publication No. 2016-188778

Non Patent Literature

NPL 1—G. Guarin, M. Hofmann, J. Nehring, R. Weigel, G. Fischer, and D. Kissinger, "Miniature Microwave Biosensors", IEEE Microwave Magazine, May 2015, pp. 71-86

SUMMARY

Technical Problem

With the foregoing in view, it is an object of embodiments of the present invention to make it possible to measure the component concentration at a high level of precision, by suppressing the influence of a change in the temperature when measuring the component concentration using the dielectric spectroscopy.

Means for Solving the Problem

Embodiments of the present invention are directed to a component concentration measuring apparatus including: a dielectric spectroscopy portion that irradiates a measurement subject with electromagnetic waves and measures a complex permittivity, thereby acquiring a dielectric spectroscopy spectrum; a temperature measurement portion that measures a temperature of the measurement subject; a correcting portion that corrects the dielectric spectroscopy spectrum according to the temperature measured by the temperature measurement portion; and a calculating portion that applies a calibration model generated in advance from a dielectric spectroscopy spectrum of a sample whose component concentration is known, to the dielectric spectroscopy spectrum corrected by the correcting portion, thereby calculating a component concentration of the measurement subject.

Furthermore, in a configuration example of the component concentration measuring apparatus according to embodiments of the present invention, a measurement probe that is arranged near the measurement subject or in contact with the measurement subject is further included, a dielectric spectroscopy sensor that transmits and receives electromagnetic waves and a temperature sensor that outputs a signal that changes in accordance with a temperature are fixed to the measurement probe such that a certain distance is interposed between the sensors, the dielectric spectroscopy portion irradiates the measurement subject with electromagnetic waves via the dielectric spectroscopy sensor, and receives electromagnetic waves from the measurement subject via the dielectric spectroscopy sensor, thereby acquiring the dielectric spectroscopy spectrum, and the temperature measurement portion converts the signal output from the temperature sensor into a temperature value.

Furthermore, in a configuration example of the component concentration measuring apparatus according to embodiments of the present invention, the correcting portion corrects the dielectric spectroscopy spectrum acquired by the dielectric spectroscopy portion, according to a time-series change in the temperature from a time when measurement of the component concentration is started.

Furthermore, embodiments of the present invention are directed to a component concentration measuring method including: a first step of irradiating a measurement subject with electromagnetic waves and measuring a complex permittivity, thereby acquiring a dielectric spectroscopy spectrum; a second step of measuring a temperature of the measurement subject; a third step of correcting the dielectric spectroscopy spectrum according to the temperature measured in the second step; and a fourth step of applying a calibration model generated in advance from a dielectric spectroscopy spectrum of a sample whose component concentration is known, to the dielectric spectroscopy spectrum corrected in the third step, thereby calculating a component concentration of the measurement subject.

Effects of Embodiments of the Invention

According to embodiments of the present invention, it is possible to suppress a change in a dielectric spectroscopy spectrum due to a temperature change using temperature information measured by a temperature measurement portion, and thus embodiments of the invention have an effect of making it possible to measure the component concentration of a measurement subject at a high level of precision even in the case of a measurement subject, such as a living body, in which the temperature changes in a relatively short period of time.

DETAILED DESCRIPTION OF ILLUSTRATIVE EMBODIMENTS

Figure 1:
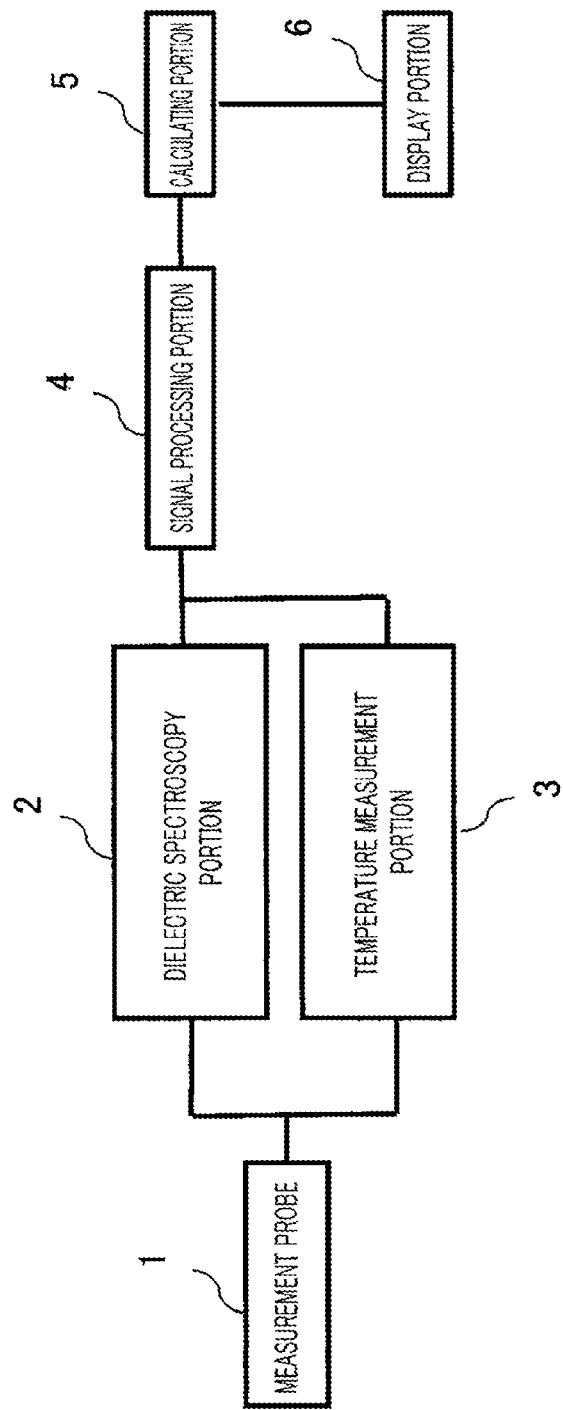
FIG. 1 is a block diagram showing the configuration of a component concentration measuring apparatus according to an embodiment of the present invention.

Hereinafter, an embodiment of the present invention will be described with reference to the figures. FIG. 1 is a block diagram showing the configuration of a component concentration measuring apparatus according to an embodiment of the present invention. The component concentration measuring apparatus shown in the figure includes a measurement probe 1 that is arranged near a measurement subject (not shown) or in contact with the measurement subject, a dielectric spectroscopy portion 2, a temperature measurement portion 3, a signal processing portion 4 (correcting portion), a calculating portion 5, and a display portion 6.

The dielectric spectroscopy portion 2 irradiates a measurement subject that is a living body, a liquid, a solid, or the like with electromagnetic waves in microwave to millimeter-wave bands, and detects electromagnetic waves reflected off the measurement subject or electromagnetic waves transmitted through the measurement subject, thereby acquiring a dielectric spectroscopy spectrum (dielectric relaxation spectrum, complex permittivity spectrum). "Living body" is a human, an animal, a cell, or the like. If the measurement subject is a human or an animal, measurement is performed while attaching the measurement probe 1 to a portion where the measurement probe 1 can be attached with ease, such as an earlobe, an arm, a palm, a leg, a belly, or the like.

Figure 2:
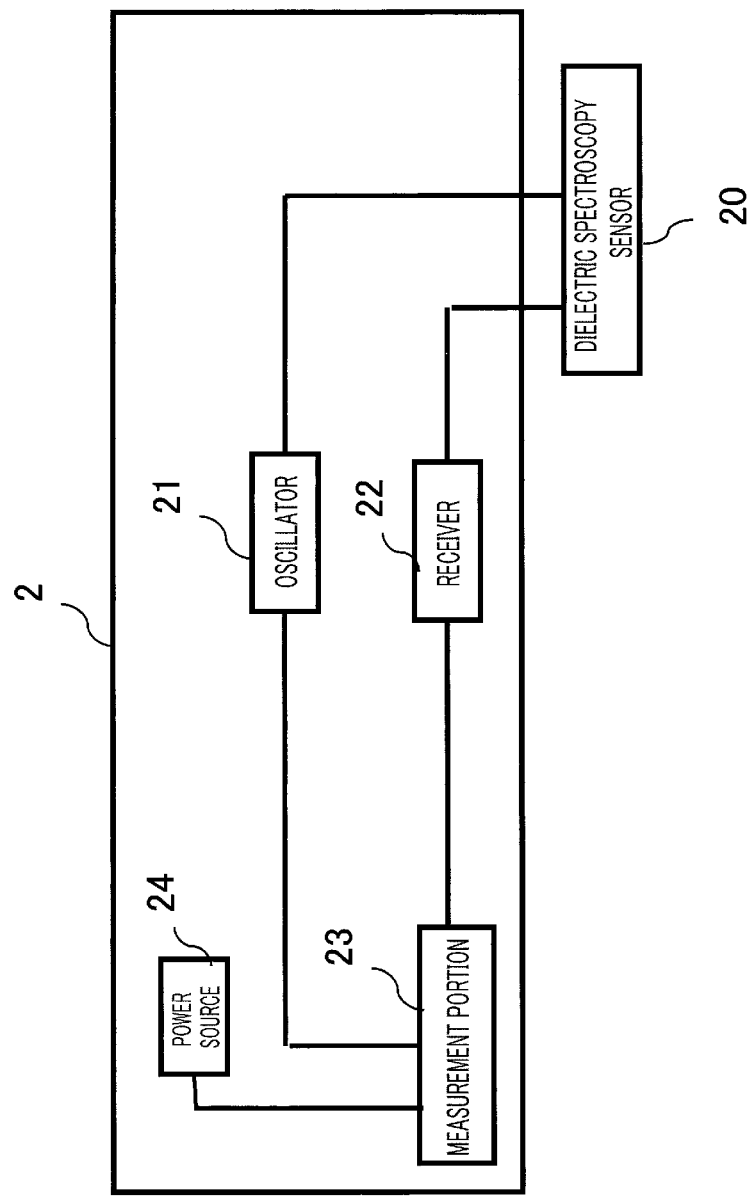
FIG. 2 is a block diagram showing a configuration of a dielectric spectroscopy portion of the component concentration measuring apparatus according to the embodiment of the present invention.

FIG. 2 is a block diagram showing the configuration of the dielectric spectroscopy portion 2. The dielectric spectroscopy portion 2 includes an oscillator 21 that supplies a signal in microwave to millimeter-wave bands to a dielectric spectroscopy sensor 20 provided in the measurement probe 1, a receiver 22 that receives electromagnetic waves reflected off the measurement subject via the dielectric spectroscopy sensor 20, a measurement portion 23 that calculates a dielectric spectroscopy spectrum from the amplitude or the phase of the electromagnetic waves received by the receiver 22, and a power source 24.

Examples of such a dielectric spectroscopy portion 2 include a vector network analyzer (VNA) and an impedance analyzer (IA).

As the dielectric spectroscopy sensor 20, a coaxial probe, a waveguide, a microstrip line, a coplanar line, and the like can be used.

As the oscillator 21, a broadband oscillator (VCO: voltage controlled oscillator), a dielectric oscillator, a synthesizer, and the like can be used. The measurement portion 23 is constituted by a microprocessor, a micro controller unit (MCU), or the like. As the power source 24, an AC adapter, a battery, or the like is used.

Figure 3:
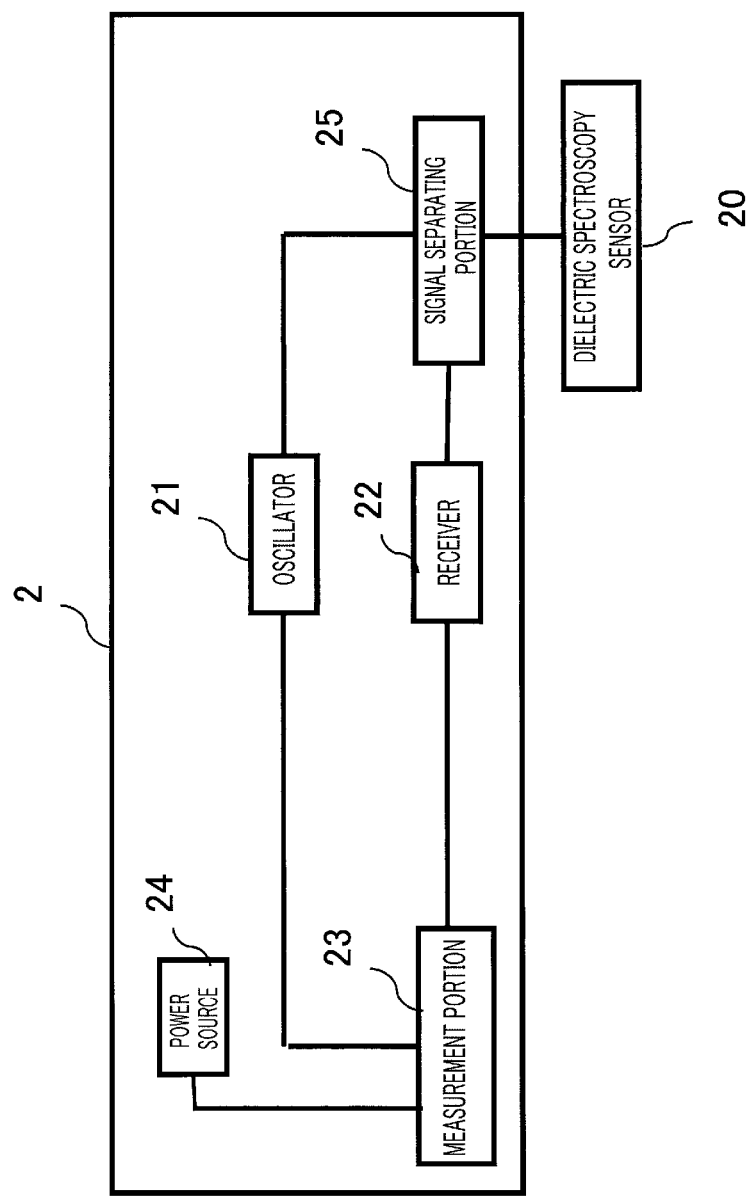
FIG. 3 is a block diagram showing another configuration of the dielectric spectroscopy portion of the component concentration measuring apparatus according to the embodiment of the present invention.

In the example shown in FIG. 2, the dielectric spectroscopy sensor 20 that independently emits and receives electromagnetic waves was described as an example. When using the dielectric spectroscopy sensor 20 that emits and receives electromagnetic waves through a common structure, it is sufficient that the dielectric spectroscopy portion 2 is provided with a signal separating portion 25 as shown in FIG. 3. The signal separating portion 25 supplies a signal from the oscillator 21 to the dielectric spectroscopy sensor 20, and outputs electromagnetic waves from the dielectric spectroscopy sensor 20 to the receiver 22. As the signal separating portion 25, a directional coupler, a circulator, and the like can be used.

The complex permittivity of a measurement subject is measured, for example, in a broadband region at 10 MHz to 70 GHz using the above-described dielectric spectroscopy portion 2.

Furthermore, instead of the dielectric spectroscopy portion 2 including a VNA or an IA, it is also possible to use a dielectric spectroscopy portion 2 including a combination of a microwave to millimeter-wave generator using two types of lasers and photo mixers, and a receiver such as a Schottky barrier diode. As the photo mixers, a PIN photodiode, an avalanche photodiode, a uni-traveling-carrier photodiode, or the like is used. As the receivers, a planar-doped barrier diode, a spectrum analyzer, a bolometer, a Golay cell, or the like may be used instead of a Schottky barrier diode. Furthermore, the free space method using a VNA and a liquid cell may be used as the permittivity measuring method. In this case, time-domain spectroscopy using a photoconductive antenna instead of a VNA or frequency-domain spectroscopy using a signal source including two types of lasers and photo mixers may be used. The dielectric spectroscopy portion 2 may be obtained by combining these plurality of methods.

Figure 4:
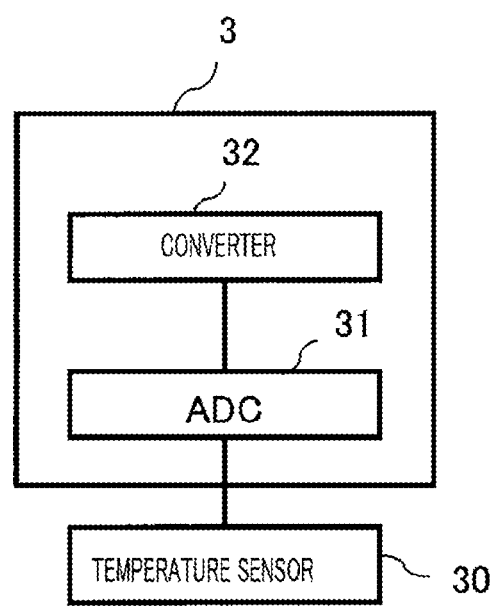
FIG. 4 is a block diagram showing the configuration of a temperature measurement portion of the component concentration measuring apparatus according to the embodiment of the present invention.

FIG. 4 is a block diagram showing the configuration of the temperature measurement portion 3. The temperature measurement portion 3 includes a temperature sensor 30 provided in the measurement probe 1, an analog-to-digital converter (ADC) 31 that converts the output of the temperature sensor 30 into a digital signal, and a converter 32 that converts the digital signal output from the ADC 31 into a temperature value.

As the temperature sensor 30, a thermocouple, a thermistor, a resistance thermometer, and the like can be used. It is also possible to provide an amplifier for amplifying a signal, a filter for removing noise, and the like between the temperature sensor 30 and the ADC 31.

The signal processing portion 4 performs pre-processing of a signal in order to improve the S/N ratio of the complex permittivity spectrum obtained by the dielectric spectroscopy portion 2. Examples of the pre-processing include processing for removing noise superimposed on a spectrum, such as averaging by measuring signals at the same frequency a plurality of times, smoothing using a moving average of a spectrum, smoothing of a spectrum using a Savitzky-Golay filter, a first derivation of a spectrum, a second derivation of a spectrum, centralization of a spectrum, scaling, multiplicative scatter correction (MSC), multiplicative scatter correction (SNV), and the like. Furthermore, the signal processing portion 4 corrects a dielectric spectroscopy spectrum according to the temperature measured by the temperature measurement portion 3. The correction will be described later in detail.

The calculating portion 5 obtains the component concentration of the measurement subject, based on the dielectric spectroscopy spectrum corrected by the signal processing portion 4. If the signal has one frequency, the calculating portion 5 performs conversion to the component concentration of the measurement subject, using a scaling factor and a bias. Furthermore, if the signal has a frequency in the form of a spectrum, the calculating portion 5 obtains the component concentration of the measurement subject, using the dielectric spectroscopy spectrum corrected by the signal processing portion 4, and a calibration model generated in advance from a sample whose component concentration is known.

The calibration model can be generated by irradiating a sample that is made of the same material as the measurement subject and whose component concentration is known, with electromagnetic waves in microwave to millimeter-wave bands, and detecting electromagnetic waves reflected off the sample, thereby acquiring a dielectric spectroscopy spectrum, and subjecting the dielectric spectroscopy spectrum to multivariate analysis. In this example, a calibration model is generated through multivariate analysis, while taking a known component concentration of a sample as a response variable, and taking a dielectric spectroscopy spectrum as an explanatory variable. Examples of the multivariate analysis method include statistical methods such as multiple regression analysis, partial least squares (PLS) regression analysis, principal-component analysis, principal-component regression, logistic regression, sparse modeling, machine learning using a neural network, and analysis methods obtained by combining these methods. It is preferable that the temperature of the sample is substantially the same as an assumed temperature of the measurement subject.

The display portion 6 displays the component concentration of the measurement subject obtained as a result of calculation by the calculating portion 5. The display portion 6 may be a display apparatus such as a liquid crystal display, or may be a computer (PC) or a smartphone connected to the calculating portion 5, for example, using Bluetooth (registered trademark).

Figure 5:
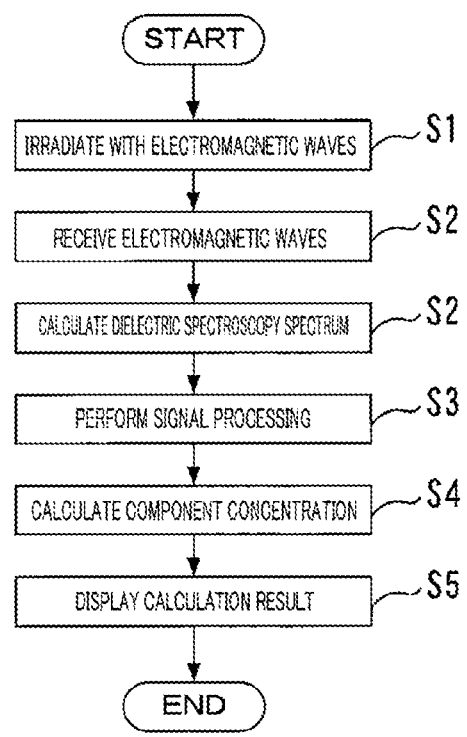
FIG. 5 is a flowchart illustrating the processing flow of the component concentration measuring apparatus according to the embodiment of the present invention.

FIG. 5 is a flowchart illustrating the processing flow of the component concentration measuring apparatus. As described above, the dielectric spectroscopy portion 2 irradiates a measurement subject with electromagnetic waves via the dielectric spectroscopy sensor 20 (step S1 in FIG. 5), receives electromagnetic waves reflected off the measurement subject via the dielectric spectroscopy sensor 20 (step S2 in FIG. 5), and calculates a complex permittivity of the measurement subject, thereby acquiring a dielectric spectroscopy spectrum (step S3 in FIG. 5).

The signal processing portion 4 performs signal processing including the above-described correction on the dielectric spectroscopy spectrum (step S3 in FIG. 5).

The calculating portion 5 calculates a component concentration of the measurement subject, based on the dielectric spectroscopy spectrum corrected by the signal processing portion 4 (step S4 in FIG. 5), and the display portion 6 displays a result of the calculation by the calculating portion 5 (step S5 in FIG. 5).

Figure 6:
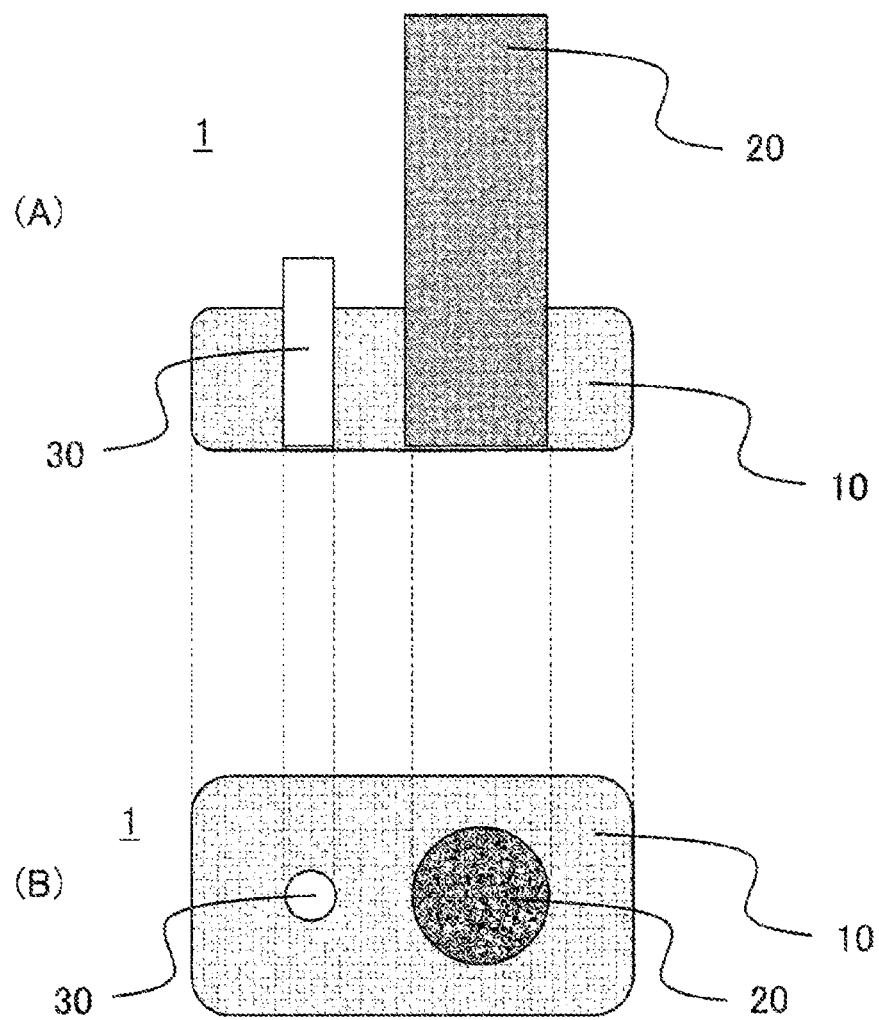
FIG. 6 shows a cross-sectional view and a bottom view showing a configuration of a measurement probe of the component concentration measuring apparatus according to the embodiment of the present invention.

FIG. 6(A) is a cross-sectional view of the measurement probe 1, and FIG. 6(B) is a bottom view of a face of the measurement probe 1 that is in contact with the measurement subject (a face that faces the measurement subject when the measurement probe 1 is arranged near the measurement subject), as viewed from the measurement subject side.

The measurement probe 1 includes a base 10, and the dielectric spectroscopy sensor 20 and the temperature sensor 30 fixed to the base 10 such that a certain distance is interposed between the sensors. The base 10 may be made of a material such as a metal (e.g., copper, silver, platinum, stainless steel, etc.) or a resin (e.g., plastic, acrylic, etc.). The shorter the distance between the dielectric spectroscopy sensor 20 and the temperature sensor 30, the better, and the distance is, for example, 5 mm or less.

Figure 7:
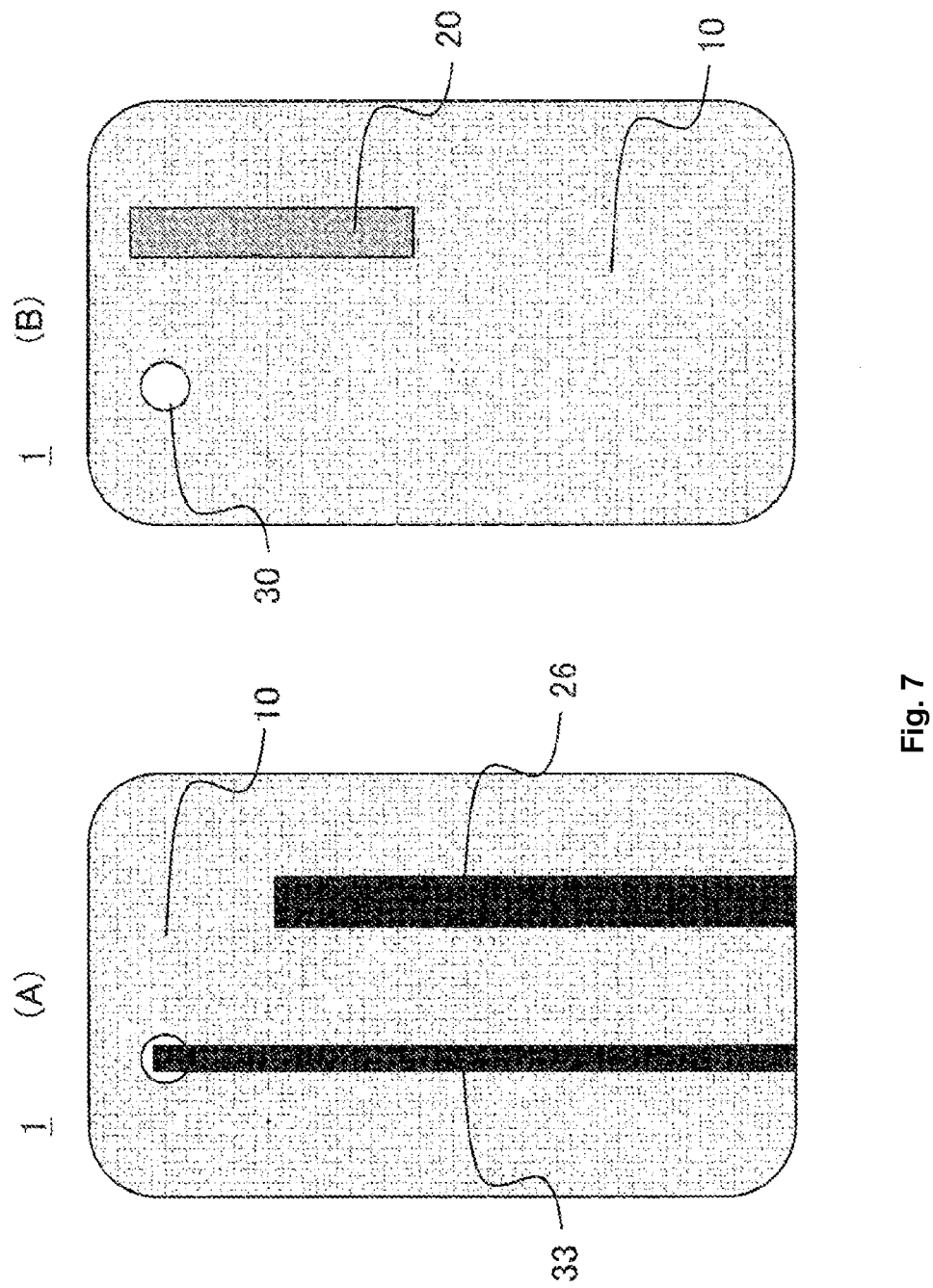
FIG. 7 shows a plan view and a bottom view showing another configuration of the measurement probe of the component concentration measuring apparatus according to the embodiment of the present invention.

FIG. 7(A) is a plan view of the measurement probe 1 as viewed from above, and FIG. 7(B) is a bottom view of the contact face of the measurement probe 1 as viewed from the measurement subject side. In the example of FIGS. 7(A) and 7(B), a base 10 in the shape of a flat plate is used, and the dielectric spectroscopy sensor 20, the temperature sensor 30, and wires 26 and 33 are integrated on the base 10. As the base 10, a printed wiring board made of glass epoxy, Teflon (registered trademark), alumina, quartz, or the like, or a flexible board made of polyimide, liquid crystal polymer (LCP), or the like may be used.

As the dielectric spectroscopy sensor 20 in FIG. 7(A) and FIG. 7(B), a structure that can be generated on a printed wiring board, such as a microstrip line, a coplanar line, a quasi-coaxial structure, or the like is used. The dielectric spectroscopy sensor 20 formed on a face of the base 10 that is in contact with the measurement subject (a face that faces the measurement subject when the measurement probe 1 is arranged near the measurement subject) and the wire 26 for external connection formed on a face of the base 10 on the side opposite to the contact face are connected to each other via a plated via hole (not shown) formed through the base 10. As the wire 26, a broadband transmission line such as a microstrip line or a coplanar line is used. Note that the via hole may be filled with a copper pin, conductive ink, or the like.

As the wire 33 for external connection of the temperature sensor 30, a structure similar to that of the wire 26 can be used. The temperature sensor 30 and the wire 33 may be connected to each other via solder, copper paste, silver paste, or the like. Furthermore, a metal wiring member made of copper, aluminum, silver, or the like may be used as the wire 33, and the wiring member may be attached to the base 10 using Kapton tape or the like.

Next, a dielectric spectroscopy spectrum that is measured by the dielectric spectroscopy portion 2 will be described. The dielectric spectroscopy spectrum obtained by the dielectric spectroscopy portion 2 is a complex number, where a real part of the complex number corresponds to a permittivity, and an imaginary part thereof corresponds to a loss of electromagnetic waves with which the measurement subject was irradiated. At this time, the dielectric spectroscopy spectrum in microwave to millimeter-wave bands is represented by Expression (1) below.

[Formula 1]

$$\varepsilon^*(\omega) - \varepsilon_\infty \sim \sum_n \frac{\Delta\varepsilon_n}{1 + i\omega\tau_n} \sim i\frac{\sigma}{\varepsilon_0\omega} \quad (1)$$

In Expression (1), $\varepsilon^*(\omega)$ is a complex permittivity of a measurement subject at each frequency $\omega$, $\varepsilon_\infty$ is a static permittivity, $\Delta\varepsilon_n$ is a relaxation strength of Debye relaxation, $\tau_n$ is a relaxation time of Debye relaxation, $\varepsilon_o$ is a permittivity of vacuum, and $\sigma$ is an electrical conductivity of a measurement subject. The first term on the right side in Expression (i) is a linear combination of a Debye relaxation model. n is the number of linear combinations, and is determined by solute and the hydration number of the solute in solvent. A real part $\varepsilon'(\omega)$ and an imaginary part $\varepsilon''(\omega)$ of the complex permittivity $\varepsilon^*(\omega)$ are defined in Expression (2) below.

[Formula 2]

$$\varepsilon^*(\omega) = \varepsilon'(\omega) - i\varepsilon''(\omega) \quad (2)$$

From the real part and the imaginary part in Expression (1) and Expression (2), $\varepsilon'(\omega)$ and $E''(\omega)$ are represented by Expressions (3) and (4) below.

[Formula 3]

$$\varepsilon'(\omega) = \varepsilon_\infty + \sum_n \frac{\Delta\varepsilon_n}{1 + (\omega\tau_1)^2} \quad (3)$$

$$\varepsilon''(\omega) = \sum_n \frac{\Delta\varepsilon_n \omega\tau_n}{1 + (\omega\tau_n)^2} + \frac{\sigma}{\varepsilon_0\omega} \quad (4)$$

An imaginary part $E''(\omega)$ of a complex permittivity represented by Expression (4) corresponds to a dielectric loss. If the measurement subject is a single component-based aqueous solution composed of molecules with a molecular weight of approximately 180, such as glucose, the dielectric spectroscopy spectrum is represented by three linear combinations as in Expression (5) below from linear combinations of a Debye relaxation model.

[Formula 4]

$$\varepsilon^*(\omega) - \varepsilon_\infty = \frac{\Delta\varepsilon_s}{1 + i\omega\tau_s} + \frac{\Delta\varepsilon_h}{1 + i\omega\tau_{hj}} + \frac{\Delta\varepsilon_b}{1 + i\omega\tau_b} \quad (5)$$

In the expression, the subscripts s, h, and b of $\Delta\varepsilon$ and $\tau$ respectively mean solute, hydrated water, and bulk water. That is to say, the first term on the right side in Expression (5) is a Debye relaxation model of solute, the second term on the right side is a Debye relaxation model of hydrated water, and the third term on the right side is a Debye relaxation model of bulk water. There may be a case in which relaxation of bulk water is divided into two types of relaxation, i.e., slow relaxation involving hydrogen bonding and rapid relaxation not involving hydrogen bonding, and a dielectric spectroscopy spectrum is represented by four linear combinations. Furthermore, if the measurement subject is an aqueous solution of protein such as lysozyme or albumin, the number of Debye relaxations regarding hydrated water increases, for example, the number of Debye relaxations may be two in the case of lysozyme and approximately 4 to 5 in the case of albumin.

In this manner, the number of linear combinations of Debye relaxations increases in accordance with the number of components of a measurement subject. When the glucose concentration increases, the level of relaxation of hydrated water due to solute and glucose increases, and the level of relaxation of bulk water decreases due to exclusion of water, and thus a spectrum change in which a peak frequency is shifted is obtained.

In Expression (1), the second term on the right side represents a conduction loss. A conduction loss is a function of electrical conductivity of a measurement subject, and the electrical conductivity mainly depends on the concentration of ions in a measurement subject or the temperature of a measurement subject. If blood, a living body, or the like is taken as a measurement subject, a spectrum based on Expression (1) in which various components are mixed is acquired.

Figure 8:
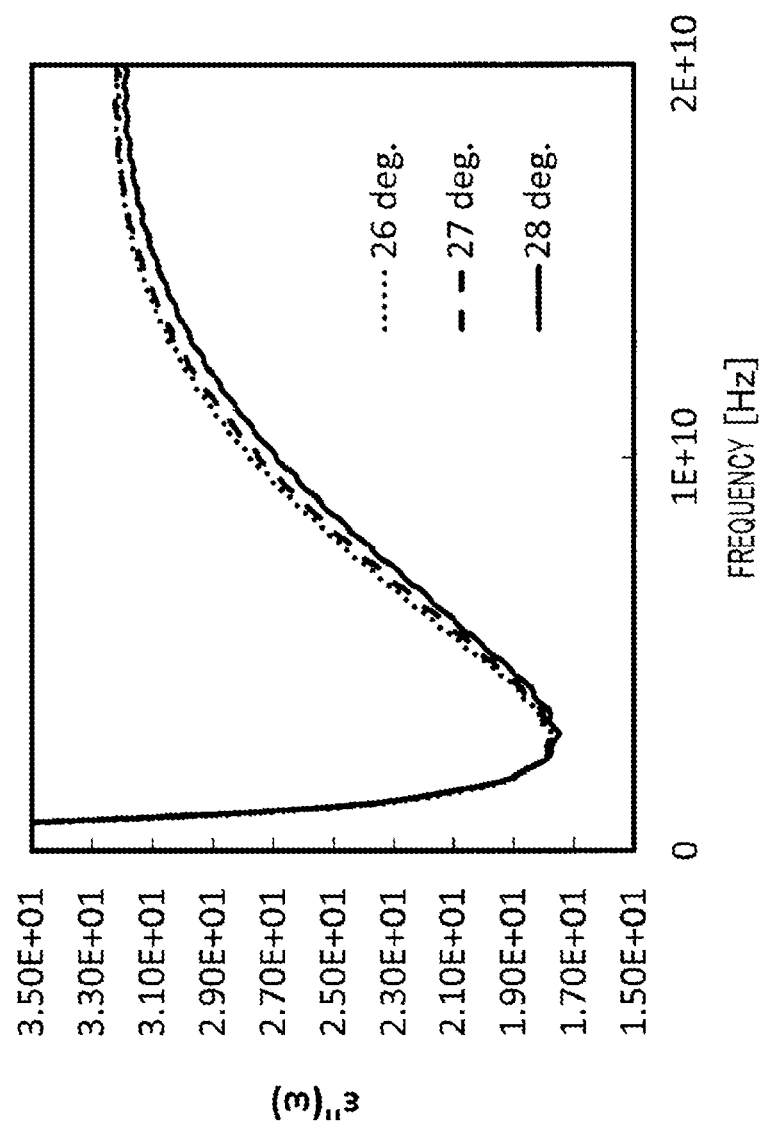
FIG. 8 is a chart showing the temperature dependency of a dielectric spectroscopy spectrum of serum.

FIG. 8 shows a temperature dependency of a dielectric spectroscopy spectrum in a case in which serum is taken as a measurement subject. In this example, dielectric spectroscopy spectra are measured in a case in which the temperature of serum is 26° C., 27° C., and 28° C. Since all of a relaxation strength $\Delta\varepsilon_n$ of Debye relaxation, a relaxation time $\tau_n$, and an electrical conductivity $\sigma$ of a measurement subject in Expression (1) depend on the temperature, when the temperature of the measurement subject changes, the dielectric spectroscopy spectrum also changes. Thus, the signal processing portion 4 of this embodiment corrects the dielectric spectroscopy spectrum using Expression (6) below, in order to reduce the influence of the temperature on the output of the dielectric spectroscopy sensor.

[Formula 5]

$$\varepsilon''_{corrected}(\omega,t)=\varepsilon''(\omega,t)+\alpha(\omega)\cdot dT(t) \quad (6)$$

In Expression (6), $\varepsilon''_{corrected}(\omega,t)$ is a corrected dielectric spectroscopy spectrum, $E''(\omega,t)$ is a dielectric spectroscopy spectrum acquired by the dielectric spectroscopy portion 2 at a time t, $\alpha(\omega)$ is a correction coefficient at each frequency, and dT(t) is a time-series change in the temperature measured by the temperature measurement portion 3. In this expression, dT(t) is defined as in Expression (7) below.

[Formula 6]

$$dT(t) = \frac{T(t)}{T_0} \quad (7)$$

In Expression (7), T(t) is a temperature measured by the temperature measurement portion 3 at a time t, and $T_o$ is a temperature measured by the temperature measurement portion 3 when measurement of the component concentration is started. dT(t) may be calculated using Expressions (8) and (9) below.

[Formula 7]

$$dT(t) = T(t) - T_0 \quad (8)$$

$$dT(t) = \frac{T(t) - T_0}{T_0} \quad (9)$$

Furthermore, it is also possible that the dielectric spectroscopy spectrum is corrected using Expression (10) below instead of Expression (6), taking the correction coefficient as a quadratic term.

[Formula 8]

$$\varepsilon''_{corrected}(\omega,t)=\varepsilon''(\omega,t)+(\alpha_1^2(\omega)+\alpha_2(\omega))\cdot dT(t) \quad (10)$$

The correction coefficient $\alpha(\omega)$ of Expression (6) and the correction coefficient $\sigma_1^2(\omega)+\alpha_2(\omega)$ of Expression (10) can be determined before starting the measurement, by performing a test that irradiates a sample that is made of the same material as a measurement subject and whose component concentration is known, with electromagnetic waves in microwave to millimeter-wave bands and acquires a dielectric spectroscopy spectrum, while changing the temperature of the sample.

Figure 9:
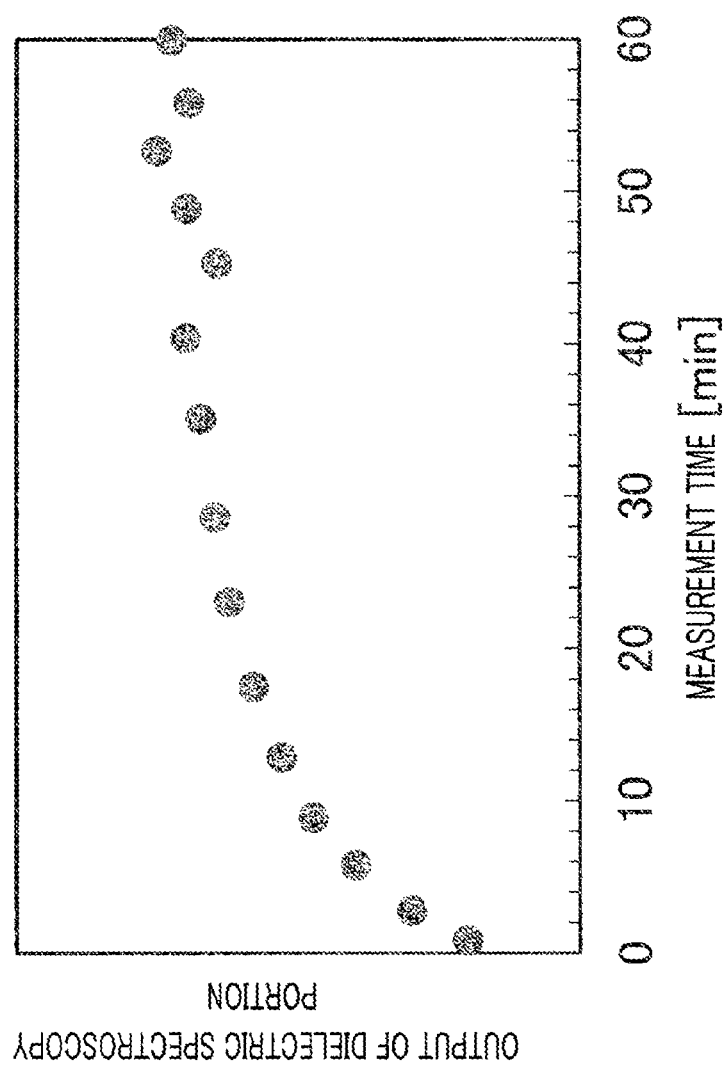
FIG. 9 is a chart showing a measurement example of dielectric spectroscopy measurement.

FIG. 9 shows an example of a time-series change in the permittivity at a frequency when dielectric spectroscopy is performed on a biological sample. It seems that, when the measurement probe 1 is placed on a measurement subject, a non-equilibrium state of the temperature appears between the measurement probe 1 and the measurement subject, which leads to two effects that the temperature changes in time series, and that, at the same time, the measurement subject is slightly heated by heat absorption of electromagnetic waves emitted from the dielectric spectroscopy portion 2.

Figure 10:
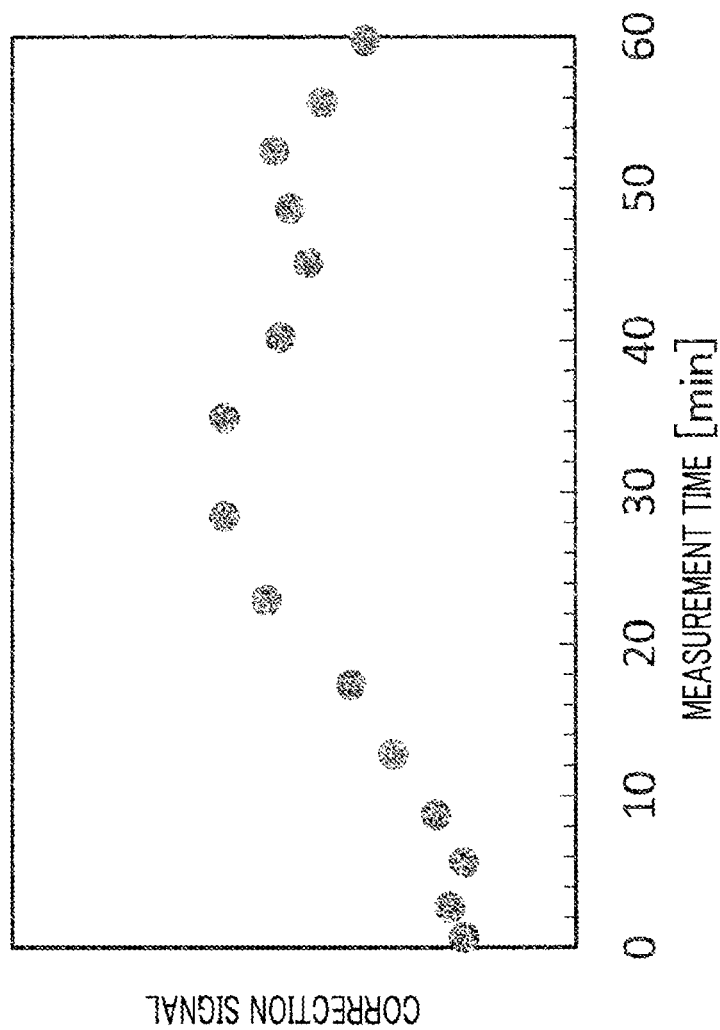
FIG. 10 is a chart showing a result obtained by performing correction of the embodiment of the present invention on the measurement example in FIG. 9.

FIG. 10 shows a result obtained by performing the correction by the signal processing portion 4 of this embodiment on the output of the dielectric spectroscopy portion in FIG. 9. With the correction of this embodiment, it is possible to suppress a change in the output of the dielectric spectroscopy portion 2 due to a change in the temperature, and to measure the amount of change in the component concentration.

The calculating portion 5 of this embodiment applies a calibration model generated in advance from a sample whose component concentration is known, to the dielectric spectroscopy spectrum corrected by the signal processing portion 4, thereby calculating a component concentration of the measurement subject. Specifically, the corrected dielectric spectroscopy spectrum is converted into the component concentration of the measurement subject using Expression (11) below.

[Formula 9]

$$C=A\cdot\varepsilon''_{corrected}(\omega,t)+B \quad (11)$$

Expression (11) is a polynomial representing a calibration model. A is a coefficient for scaling, and B is bias. If $\varepsilon''_{corrected}(\omega,t)$ is a spectrum, the first term on the right side of Expression (11) is an inner product of the coefficient and the corrected dielectric spectroscopy spectrum, and a higher level of precision can be expected through methods such as signal processing or multivariate analysis performed by the signal processing portion 4 or the calculating portion 5.

As described above, according to this embodiment, a dielectric spectroscopy spectrum of a measurement subject such as a living body is acquired using the dielectric spectroscopy portion 2 that can measure the complex permittivity in MHz to GHz bands and the temperature measurement portion 3 that can measure the temperature in a state in which the dielectric spectroscopy sensor 20 and the temperature sensor 30 are located close to each other, and a change in the dielectric spectroscopy spectrum due to a temperature change is suppressed using the temperature information. Thus, it is possible to measure the component concentration of a measurement subject at a high level of precision even in the case of a measurement subject, such as a living body, in which the temperature changes in a relatively short period of time.

Figure 11:
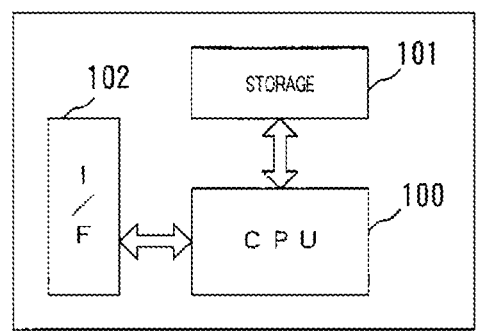
FIG. 11 is a block diagram showing a configuration example of a computer that realizes the component concentration measuring apparatus according to the embodiment of the present invention.

The signal processing portion 4 and the calculating portion 5 of the component concentration measuring apparatus described in this embodiment can be realized by a computer including a central processing unit (CPU), a storage, and an interface, and a program for controlling these hardware resources. FIG. 11 shows a configuration example of the computer. The computer includes a CPU 100, a storage 101, and an interface (hereinafter, abbreviated as an "I/F") 102. In this computer, a program for realizing the component concentration measuring method according to embodiments of the present invention is stored in the storage 101. The CPU 100 executes the processing described in this embodiment according to the program stored in the storage 101. Note that a computer that realizes the measurement portion 23 of the dielectric spectroscopy portion 2 may be the same as the computer that realizes the signal processing portion 3 and the calculating portion 4, or a computer that is different therefrom.

INDUSTRIAL APPLICABILITY

Embodiments of the present invention can be applied to component concentration measurement using the dielectric spectroscopic technique.

REFERENCE SIGNS LIST

1 Measurement probe
2 Dielectric spectroscopy portion
3 Temperature measurement portion
4 Signal processing portion
5 Calculating portion
6 Display portion
10 Base
20 Dielectric spectroscopy sensor
21 Oscillator
22 Receiver
23 Measurement portion
24 Power source
25 Signal separating portion
26, 33 Wire
30 Temperature sensor
31 Analog-to-digital converter
32 Converter.

The invention claimed is:

1. A component concentration measuring apparatus comprising:
a dielectric spectroscopy portion that irradiates a measurement subject with first electromagnetic waves and measures a complex permittivity to acquire a dielectric spectroscopy spectrum;
a temperature measurement portion that measures a temperature of the measurement subject;
a correcting portion that corrects the dielectric spectroscopy spectrum according to the temperature measured by the temperature measurement portion and a temperature correction coefficient, the temperature correction coefficient being determined in advance from a sample dielectric spectroscopy spectrum of a sample, wherein the sample dielectric spectroscopy spectrum of the sample is acquired by irradiating the sample while changing a temperature of the sample and while irradiating the sample with electromagnetic waves across a plurality of wavelengths; and
a calculator that applies a calibration model to the dielectric spectroscopy spectrum corrected by the correcting portion to calculate a component concentration of the measurement subject, wherein the calibration model is generated in advance from a dielectric spectroscopy spectrum of a sample with a known component concentration.

2. The component concentration measuring apparatus according to claim 1, further comprising:
a measurement probe, wherein a dielectric spectroscopy sensor that transmits and receives electromagnetic waves and a temperature sensor that outputs a signal that changes in accordance with a temperature are fixed to the measurement probe such that a certain distance is interposed between the dielectric spectroscopy sensor and the temperature sensor, wherein the dielectric spectroscopy portion irradiates the measurement subject with the first electromagnetic waves via the dielectric spectroscopy sensor and receives second electromagnetic waves from the measurement subject via the dielectric spectroscopy sensor to acquire the dielectric spectroscopy spectrum, and wherein the temperature measurement portion converts a signal output from the temperature sensor into a temperature value.

3. The component concentration measuring apparatus according to claim 2, wherein the measurement probe is placed in direct contact with the measurement subject.

4. The component concentration measuring apparatus according to claim 2, wherein the measurement probe is physically separated from the measurement subject.

5. The component concentration measuring apparatus according to claim 1, wherein the correcting portion corrects the dielectric spectroscopy spectrum acquired by the dielectric spectroscopy portion, according to a time-series change in the temperature, the time-series change in the temperature being from a time when measurement of the component concentration is started.

6. The component concentration measuring apparatus according to claim 1, wherein the sample is made of the same material as a measurement subject, and wherein a component concentration of the sample is known.

7. The component concentration measuring apparatus according to claim 1, wherein irradiating the sample with the electromagnetic waves across the plurality of wavelengths comprises irradiating the sample with electromagnetic waves in microwave to millimeter-wave bands.

8. A component concentration measuring method comprising:
irradiating a measurement subject with electromagnetic waves;
measuring a complex permittivity to acquire a dielectric spectroscopy spectrum of the measurement subject;
measuring a temperature of the measurement subject;
correcting the dielectric spectroscopy spectrum according to the temperature of the measurement subject and a temperature correction coefficient, the temperature correction coefficient being determined in advance from a sample dielectric spectroscopy spectrum of a sample, wherein the sample dielectric spectroscopy spectrum of the sample is acquired by irradiating the sample while changing a temperature of the sample and while irradiating the sample with electromagnetic waves across a plurality of wavelengths; and
applying a calibration model to the dielectric spectroscopy spectrum corrected according to the temperature of the measurement subject to calculate a component concentration of the measurement subject, wherein the calibration model is generated in advance from a dielectric spectroscopy spectrum of a sample having a known component concentration.

9. The component concentration measuring method according to claim 8, wherein irradiating the measurement subject with the electromagnetic waves and measuring the temperature of the measurement subject comprises using a measurement probe, to which a dielectric spectroscopy sensor that transmits and receives electromagnetic waves and a temperature sensor that outputs a signal that changes in accordance with a temperature are fixed such that a certain distance is interposed between the dielectric spectroscopy sensor and the temperature sensor.

10. The component concentration measuring method according to claim 9, measuring the complex permittivity to acquire the dielectric spectroscopy spectrum of the measurement subject comprises receiving electromagnetic waves from the measurement subject via the dielectric spectroscopy sensor.

11. The component concentration measuring method according to claim 9, wherein measuring the temperature of the measurement subject comprises converting a signal output from the temperature sensor into a temperature value.

12. The component concentration measuring method according to claim 9, wherein the measurement probe is placed in direct contact with the measurement subject while irradiating the measurement subject with the electromagnetic waves and measuring the temperature of the measurement subject.

13. The component concentration measuring method according to claim 9, wherein the measurement probe is placed is physically separated from the measurement subject while irradiating the measurement subject with the electromagnetic waves and measuring the temperature of the measurement subject.

14. The component concentration measuring method according to claim 8, wherein correcting the dielectric spectroscopy spectrum comprises correcting the dielectric spectroscopy spectrum according to a time-series change in the temperature, the time-series change in the temperature being from a time when measurement of the component concentration is started.

15. The component concentration measuring method according to claim 8, wherein the sample is made of the same material as a measurement subject, and wherein a component concentration of the sample is known.

16. The component concentration measuring method according to claim 8, wherein irradiating the sample with the electromagnetic waves across the plurality of wavelengths comprises irradiating the sample with electromagnetic waves in microwave to millimeter-wave bands.

\* \* \* \* \*